US008095204B2

(12) United States Patent
Smith et al.

(10) Patent No.: US 8,095,204 B2
(45) Date of Patent: Jan. 10, 2012

(54) APPARATUS AND METHOD FOR DIAGNOSING BREAST CANCER INCLUDING EXAMINATION TABLE

(75) Inventors: Randall M. Smith, Glenview, IL (US); Jack E. Bridges, Park Ridge, IL (US); Denis E. Jones, II, Arlington Heights, IL (US); Todd R. Henry, Arlington Heights, IL (US)

(73) Assignee: Interstitial, LLC, Mt. Prospect, IL (US)

( * ) Notice: Subject to any disclaimer, the term of this patent is extended or adjusted under 35 U.S.C. 154(b) by 1293 days.

(21) Appl. No.: 10/637,221

(22) Filed: Aug. 8, 2003

(65) Prior Publication Data

US 2004/0097811 A1    May 20, 2004

Related U.S. Application Data

(60) Provisional application No. 60/402,511, filed on Aug. 9, 2002.

(51) Int. Cl.
*A61B 5/00* (2006.01)

(52) U.S. Cl. .............................. 600/430; 324/637; 5/601

(58) Field of Classification Search .................. 600/430, 600/407; 324/637; 5/601
See application file for complete search history.

(56) References Cited

U.S. PATENT DOCUMENTS

| | | | |
|---|---|---|---|
| 4,641,659 A | | 2/1987 | Sepponen |
| 4,774,961 A | * | 10/1988 | Carr .............................. 600/549 |
| 5,168,514 A | * | 12/1992 | Horton et al. .................. 378/209 |
| 5,704,355 A | | 1/1998 | Bridges |
| 5,807,257 A | | 9/1998 | Bridges |
| 5,829,437 A | | 11/1998 | Bridges |
| 5,841,288 A | | 11/1998 | Meaney et al. |
| 5,983,124 A | | 11/1999 | Carr |
| 6,061,589 A | | 5/2000 | Bridges et al. |
| 6,421,550 B1 | | 7/2002 | Bridges et al. |
| 6,448,788 B1 | * | 9/2002 | Meaney et al. ............... 324/637 |
| 6,454,711 B1 | * | 9/2002 | Haddad et al. ................ 600/371 |

(Continued)

OTHER PUBLICATIONS

Alan W. Preece, et al., Dielectric Imaging for Localisation & Detection of Breast Tumours, 1993 IEEE MTT-S Digest, pp. 1145-1146.

(Continued)

*Primary Examiner* — Brian Casler
*Assistant Examiner* — Amanda Lauritzen
(74) *Attorney, Agent, or Firm* — Fitch, Even, Tabin & Flannery

(57) ABSTRACT

A microwave breast cancer imaging method that includes an examination table that is both comfortable and reliable is provided that includes a support system and an orientation system such that breasts can remain in a fixed position to allow for scanning. A horizontal microwave and optically transparent scan plate forms part of the top of the examination table. The imprint of the breasts on the scan plate may be visually displayed to aid in the orienting of each breast such that all volumes within the breast are scanned. Microwave power is then scanned upward through the scan plate to develop a microwave response that is indicative of the presence of a lesion. After scanning, the visual imprint of the breast is recorded. As needed, microwave equipment can be included within a microwave shielded enclosure that also forms part of the scan table. Spurious leakage of microwave power may be further suppressed by use of microwave-absorbing materials, within the enclosure and, in the padding that covers the surface of the examination table and removable pads.

52 Claims, 8 Drawing Sheets

U.S. PATENT DOCUMENTS

| | | | |
|---|---|---|---|
| 6,470,217 | B1 | 10/2002 | Fenn et al. |
| 7,825,667 | B2 * | 11/2010 | Fang et al. .................. 324/637 |
| 2004/0077943 | A1 * | 4/2004 | Meaney et al. ............... 600/430 |
| 2005/0107692 | A1 * | 5/2005 | Li et al. ........................ 600/430 |
| 2005/0251018 | A1 * | 11/2005 | Gleman ........................ 600/407 |
| 2006/0241409 | A1 * | 10/2006 | Winters et al. ............... 600/430 |
| 2006/0241410 | A1 * | 10/2006 | Fang et al. ................... 600/430 |
| 2011/0054294 | A1 * | 3/2011 | Kruger ......................... 600/407 |

OTHER PUBLICATIONS

E.C. Fear et al., Confocal Microwave Imaging for Breast Tumor Detection; Comparison of Immersion Liquids, Antennas and Propagation Society, 2001 IEEE Intl. Sym., pp. 250-253, vol. 1.

E. Falchi, et al., A New Microwave Scanning System for Imaging Superficial Organs, Journal of Nuclear Medicine & Allied Sciences, vol. 29, No. 3, 1985, pp. 275-282.

E.C. Gregg et al., A Microwave Scanner for Soft Tissue Tumor Detection, Case Western Reserve University, Dept. of Radiology, Cleveland, OH, SPIE, vol. 152, 1978, pp. 104-108.

P.A. Meaney et al., A Clinical Prototype for Active Microwave Imaging of the Breast, IEEE Transactions on Microwave Theory & Techniques, vol. 48, No. 11, Nov. 2000, pp. 1841-1853.

E.C. Fear et al., Microwave Detection of Breast Cancer, IEEE Transactions on Microwave Theory &Techniques, vol. 48, No. 11, Nov. 2000, pp. 1854-1863.

* cited by examiner

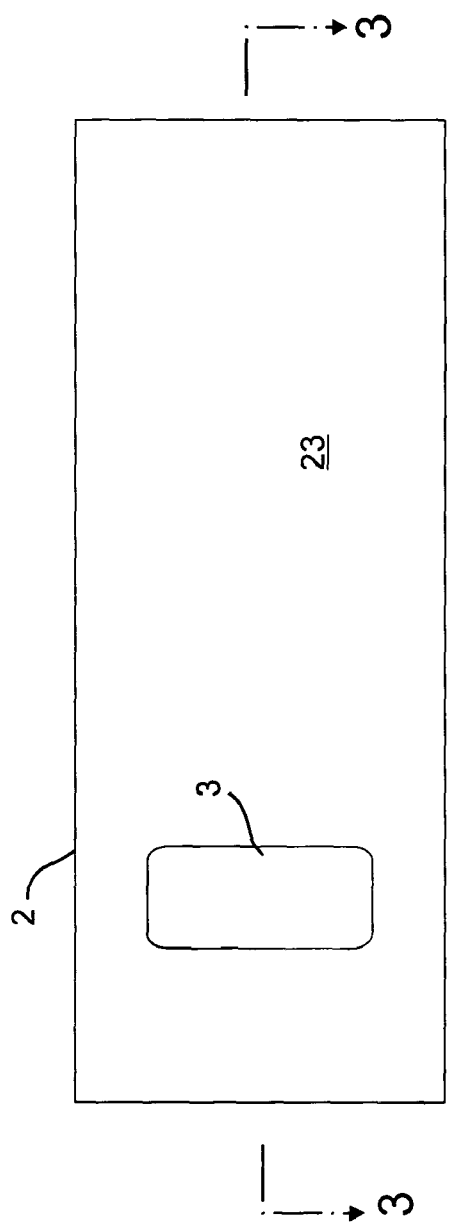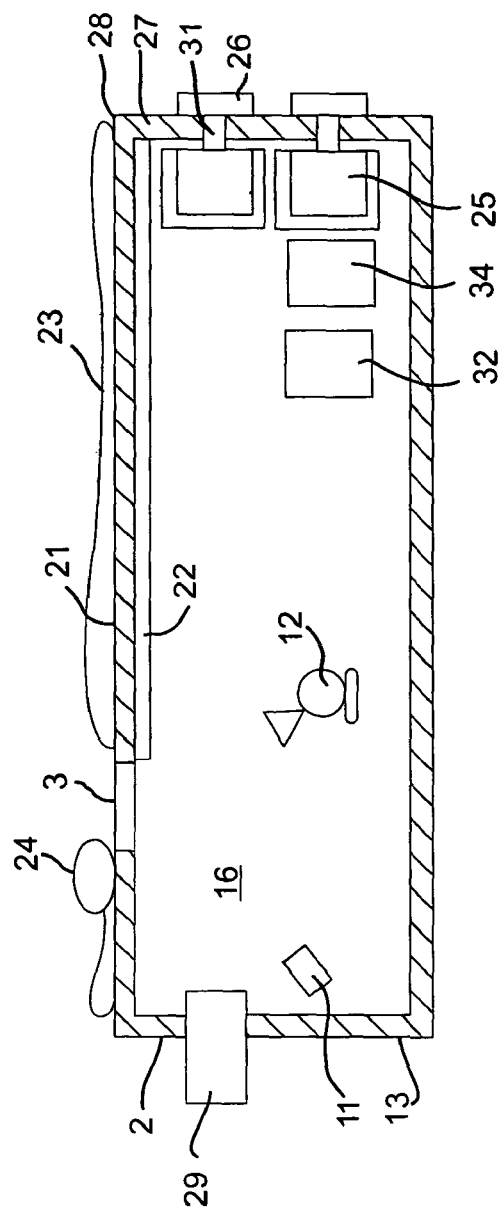

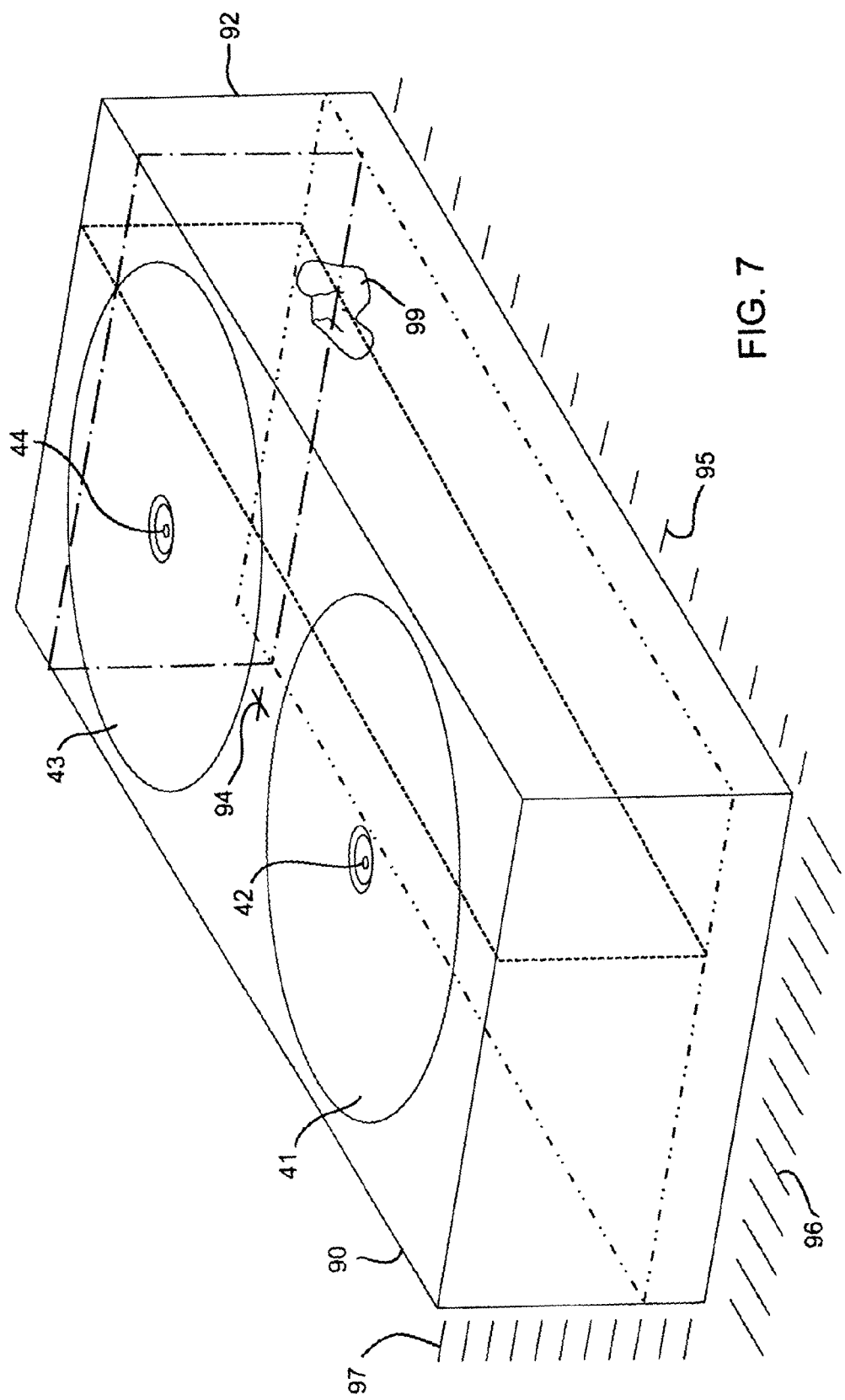

APPARATUS AND METHOD FOR DIAGNOSING BREAST CANCER INCLUDING EXAMINATION TABLE

This application claims the benefit of the filing date of co-pending provisional application Serial No. 60/402,511, filed Aug. 9, 2002.

BACKGROUND

The present invention pertains to a medical examination apparatus and method for detecting breast cancer. In particular, the present invention pertains to an examination table having scanning equipment, including microwave equipment and features to aid in screening or diagnosis of breast cancer.

Breast cancer is a major health problem for women. While early detection leads to improved treatment and increased longevity, the existing low-cost screening methods leave much to be desired. For example, as many as 10 to 30% of the malignant tumors in mammogram-screened women go undetected. The result is that about 16,000 women who annually have a mammogram will have a malignant tumor and not know it. Some 20 million women annually fail to comply with the American Cancer Society recommendations for annual mammograms and about 120,000 of these women develop late stage, difficult-to-treat breast cancer. The reasons for the non-compliance are, in part, that mammography is physically uncomfortable, provides uncertain results and poses an ionizing radiation risk. The physical discomfort from mammograms arises because 40% of the tumors occur near the armpit or axilla. Thus, the breast must be compressed between two plates to assure that the tumors near the armpit are imaged. The excess treatment costs for these 120,000 unscreened women are on the order of several billion dollars and the social costs are high in terms of reduced longevity and impaired life style.

A number of novel electromagnetic systems have been investigated that addresses these problems on an analytical and small-scale laboratory basis. However, these have not considered how the patient can be comfortably, safely and reliably examined by physicians on a routine basis to screen women or diagnose women for breast cancer.

Both low-frequency and microwave systems have been or are being considered. These systems detect the high water content of the malignant tumors or lesions that are embedded in the low-water-content normal breast tissues. While some of these systems have been demonstrated theoretically or in small-scale laboratory tests, no provision for large-scale, reliable and comfortable examinations has been noted.

For example, a low-frequency, electrical-impedance measurement system was commercially offered that determined the presence of a malignant tumor. For this, a hand-held sensor with exposed electrodes was physically drawn across the surfaces of the breast. This low-frequency system measured the impedance variations between electrodes that are in physical contact with the surface of the breast. For this, the patient lies on her back and the electrodes are indexed over the surface of the breast. This technique required physically manipulating the breast and this introduced uncertainties as to the location of the electrodes and lead to uncertain results. These uncertain results caused this low-frequency method to be subsequently abandoned.

In another version, the electrodes are all located on a flat plate that is pressed against the breast and may not detect tumors or lesions near the armpit or periphery of the plate. A major difficulty with these low-frequency techniques is that the results require considerable training to correctly diagnose the results of the measurements.

A microwave method applied unfocused 900 megahertz energy directly to the breast via a resonant, open-faced, microwave cavity. The cavity was hand held and was repositioned at different locations over both of the breasts. By comparing the data from one breast with the other, some tumors were found in older women, except for tumors near the nipples. Tumors in younger women were not detected. Beyond these initial tests, no further work was reported.

A concept for a 10 GHz, continuous-wave microwave beam is disclosed in Sepponen U.S. Pat. No. 4,641,659, to scan the breast via a dielectric plate that is pressed against the breast. The beam is developed from an open-ended waveguide antenna that is mechanically scanned across the dielectric plate to form a 2-D image of the backscattered perturbations that might come from a tumor. Sepponen recommends dielectric materials of the scan plate to match the dielectric properties of the normal breast tissue. While some matching is beneficial in Sepponen's case this match must be precise in order to avoid reflections that could mask the desired returns. This is difficult, especially over a wide bandwidth, for both the dielectric constant and the conductivity. However, such values are only commercially available in visually opaque materials (Emerson Cuming). The matching concept alone is impractical because the dielectric properties of the breast vary widely, and these are a function of the patient's age, menses, lactation, and weight. This mismatch will create reflections that mask the desired returns. Sepponen is silent as to how the breast can be comfortably held in a fixed position for the several minutes needed to conduct a scan and does not disclose a support system. Further, means or methods are not described where tumors or lesions near the armpit are detected. Also, Sepponen does not provide a means to record the location of a tumor or lesion relative to the imprint of the breast on the dielectric plate, which may be needed for subsequent treatment of the tumor. Finally, Sepponen does not disclose an orientation system.

Many microwave, infrared and optical systems have been proposed to detect breast tumors that use an examination table with a hole in the table where the breast hangs pendent in a test chamber. Microwave, infrared or optical energy is propagated through the breast and the scattered energy is collected by sensors surrounding the pendent breast. The microwave approach is exempflied by Meany ("A Clinical Prototype For Active Microwave Imaging of the Breast," P. Meany, M. Fanning, D. Li, S. Poplack, K. Paulsen; IEEE Transactions on Microwave Theory and Techniques, Vol. 48, No. 11, November 2000). Fear ("Microwave Detection of Breast Cancer," E. C. Fear, M. A. Stuchy; IEEE Transactions on Microwave Theory and Technique, Vo. 48, No. 11, November 2000) has proposed an alternative microwave breast tumor imaging system that beams microwave energy through the breast. Meaney's system employs an iterative technique to develop spatial distribution of the conductivity within the breast. Fear employs imaging techniques similar to those described in patents developed by this applicant, such as in U.S. Pat. No. 5,704,355. To do the scan through the breast, the woman lies face down on an examination table so that her breast hangs pendent in a test chamber that is sometimes filled with water or other liquids. This arrangement also misses tumors near the armpit. A major difficulty with these methods is that the surface of the breast is not well defined with respect to the locations of the antennas that are positioned around the breast. This increases computational complexity and may lead to diagnosis problems.

Wide band, confocal pulsed microwave imaging has been proposed and described in U.S. Pat. Nos. 5,704,355 5,807,257 5,829,437 and 6,061,589. These employ a scan plate that is placed on the surface of the breast of a patient lying on her back. To demonstrate feasibility, a microwave, wide band of 1 to 10 GHz, confocal, pulsed microwave breast cancer 3-D imaging system has been developed that successfully images tumors in 3-D in human breast tissues that were not otherwise detectable in mammograms. For these human tests, the patient lies on her back with a microwave transparent dielectric material lightly positioned on her breast. A small, handheld antenna, positioned in known locations, both illuminates the breast and collects the backscatter at each location. Data from all of the locations is then digitally processed to form a 3-D image. This system, while satisfactory for preliminary tests, requires substantial examination times and would need substantial training of the attending technician to hold the scan plate steady and to precisely define the antenna positions with respect to the anatomy of the patient.

The technical foundation behind this device has been disclosed under the following US patents and are hereby incorporated by reference: Non Invasive System for Breast Cancer Detection, U.S. Pat. No. 5,704,355 (Jan. 6, 1998), J. E. Bridges; Breast Cancer Detection, Imaging and Screening by Electromagnetic Millimeter Waves U.S. Pat. No. 5,807,257 (Sep. 15, 1998), J. E. Bridges; Microwave Method and System to Detect and Located Cancers in Heterogeneous Tissues, U.S. Pat. No. 5,829,437 (Nov. 3, 1998), J. E. Bridges; Microwave Antennas for Cancer Detection System, U.S. Pat. No. 6,061,589 (May 9, 2000), Jack E. Bridges, et. al; Microwave Antennas for Cancer Detection System, U.S. Pat. No. 6,061,589 (May 9, 2000), Jack E. Bridges, et. al; and Microwave Discrimination Between Malignant and Benign Breast Tumors, U.S. Pat. No. 6,421,558 (Jul. 16, 2002), Jack E. Bridges, et al.

The aforementioned microwave systems require improvements for routine screening, such as by technicians or for clinical, or diagnostic use by the physicians. A number of novel features, heretofore not available are needed and are provided by the present invention.

SUMMARY OF THE INVENTION

The present invention provides for an apparatus including an examination table to be used in a clinical setting, to provide screening and imaging of breast anomalies in a way that is safe, simple, comfortable, convenient and effective. In an embodiment, the apparatus is configured as an examination table. In an embodiment, the present invention provides for an apparatus for screening or diagnosing cancer or other pathological disorders, such as in a breast of a patient, comprising a table having a horizontal upper surface upon which the patient may lie, a support system to support the breast of the patient comfortably in a fixed position, a microwave assembly comprising a microwave antenna including a microwave source and receiver subsytsem for detecting said reflected microwave signals from the breast under examination, an orientation system for orienting a surface of the breast in known positions with respect to the anatomy of the patient and locations of the antenna and a processor connected to said receiver for processing said reflected microwave signal.

In an embodiment, the support system includes a microwave-transparent scan plate carried by the table. In an embodiment, the scan plate may be optically transparent and the orientation system may further comprise a light source oriented to transmit light through the scan plate in order to optically illuminate the breast and a camera for capturing a visual image of the breast and transmitting said image to the processor and a displayed image received from the processor including the visual image.

In an embodiment, the orientation system may further include a scan data system for providing a scan image from the processed reflected microwave energy, the scan data system may be connected to the processor and a display for displaying the scan image of the reflected microwave energy. In an embodiment, the orientation system may further comprise a means for displaying an overlay of the visual image and the scan image of the processed reflected microwave energy. In an embodiment, the support system may include a microwave-transparent scan plate located in the upper surface so that the breast may be pressed against the plate. In an embodiment, the support system may include a microwave-absorbent resilient member located adjacent the scan plate and interposed between the patient and the upper surface of the table. In an embodiment, the support system may include an enclosure formed by the table.

In an embodiment, the apparatus may further include a scan plate with a dielectric constant in the range of from about 1.7 to about 9. In an embodiment, the apparatus may further produce a composite image that is a 3-D image. In an embodiment, the apparatus may further have the positioning of the breast on the scan plate to provide for a microwave antenna position that is stable within approximately ¼th of a wavelength of the highest frequency in normal breast tissue. In an embodiment, the apparatus may further have an air gap of approximately 1 mm between the antenna and the scan plate. In an embodiment, the microwave absorbent resilient member may be a bag-like pillow. In an embodiment, the microwave absorbent resilient member may be a collar. In an embodiment, the microwave absorbent resilient member may form a padding layer on the upper surface. In an embodiment, the processor may be a personal computer incorporated with the table. In an embodiment, the personal computer may provide a display for the displayed image. In an embodiment, the processor may be provided within the enclosure of the table. In an embodiment, the camera may be a digital camera. In an embodiment, the apparatus may include a motorized system for moving the antenna along X-Y coordinates.

In a further embodiment, the present invention provides for a method for imaging or detecting breast tumors comprising the steps of having a patient lie prone on a table having a transparent scan plate, pressing a patient's breast against the scan plate, illuminating the patient's breast through the scan plate, receiving a visual image of the breast by a digital camera, scanning the breast with microwave antennae, receiving the scanned data by a processor and forming a displayed image including the visual image and the processed scanned data.

In an embodiment, the method may further provide for a pair of breasts being imaged. In an embodiment, the method may further provide for the patient being oriented in order to provide a frontal imprint of the breast. In an embodiment, the method may further provide for the patient being oriented in order to provide a side imprint of the breast near the patient's armpit. In an embodiment, the method may further provide for the step of archiving the displayed image. In an embodiment, the method may further include for the step of analyzing the visual display and reorienting the patient in order to provide the breasts in appropriate orientation. In an embodiment, the method may further provide for the analyzing to be performed by a human viewing the visual display.

In an embodiment, the method may further provide for the step of identifying areas of the breast to be scanned by the antenna. In an embodiment, the method may further provide for the identifying to be performed by a human technician using a mouse with a computer displaying the displayed image. In an embodiment, the method may further provide for the step of orienting a microwave-absorbent resilient member adjacent the patient in order to cover areas of the scan plate that are beyond the breast. In an embodiment, the method may further provide for the microwave absorbent resilient member to be a bag-like pillow.

In an embodiment, the table may include a microwave and optically transparent window or scan plate. Beneath the scan plate may be an antenna that is used to transmit and receive radio frequency signals. In addition, the antenna, microwave source and receiver, digital camera, scan plate, spot lights, and other electronic and electrical equipment can be, if needed, housed in a metallic envelope which is lined with microwave-absorbing material. In an embodiment, microwave suppressing power line, data line and air vent devices may be housed within the examination table. To conduct an imaging scan, the patient may lie on the table, either face down or on her side, with either the nipple area of the breast or armpit area of her body in contact with the scan plate. The technician may illuminate the imprint of the breast(s) on the scan plate and the digital camera records the imprint. These data may then be displayed and the technician determines if the breast(s) are properly positioned.

The imprint may also be viewed by the technician to note any gaps between the torso and the scan plate. As needed, these gaps may be blocked with microwave-absorbing material. A technician may then use a control screen and keyboard of the controlling computer to initiate an automated scanning procedure. In an embodiment, an antenna or other illumination means may be located below the plate with the element facing upwards. It may be moved through a number of known and discrete locations across the scan plate and may be indexed through a discrete number of locations or antenna positions across the scan plate. The computer may execute the applications required to complete the scanning procedure and display the processed scan results.

The stability of the surface of the breast, and the relative positions between the breast surface and the antenna positions may be maintained throughout the scan procedure. These requirements enable the system to post-process the signal return data and develop and display a three-dimensional image of the internal breast volume with any detected anomalies highlighted. In an embodiment, the examination table my be designed such that when the patient lies in contact with the scan plate, almost all of the spurious microwave leakage that might be passed through the scan plate opening in the shielded examination table is absorbed by the upper torso of the patient. The padding near the scan plate and any pillows or collars needed to position the patient may be filled with soft, pliable microwave-absorbing material.

In a further embodiment of the invention an examination table is provided comprising a table having a horizontal upper surface upon which the patient may lie, a support system to support the patient comfortably in a fixed position and an orientation system to orient the surface of the patient's torso in known positions with respect to the anatomy of the patient. In an embodiment, the support system may include an optically transparent scan plate and further comprising a light source oriented to transmit light through the scan plate in order to optically illuminate the torso, a camera for capturing a visual image of the torso and transmitting said image to a processor and means coupled to the processor for displaying an image including the visual image of the torso's imprint. In an embodiment, the table may include an adjustable upper surface section to aid the patient to sit upright. In an embodiment, the table may include a removable pad. In an embodiment, the removable pad may cover the scan plate. In an embodiment, the removable pad may include a taper in order to appropriately elevate the patient's torso in order to comfortably locate the torso on the scan plate. In an embodiment, the removable pad may provide an adjustable upper surface section of the table. In an embodiment, the orientation system may includes a scan system for providing scan data regarding the patient's breast with respect to at least breast tissue, a nipple, a sternum, an armpit or a lesion.

BRIEF DESCRIPTION OF THE DRAWINGS

For the purpose of facilitating an understanding of the subject matter sought to be protected, there are illustrated in the accompanying drawings embodiments thereof, from an inspection of which, when considered in connection with the following description, the subject matter sought to be protected, its construction and operation, and many of its advantages should be readily understood and appreciated.

FIG. 2 is a top plan view of an examination table of the present invention;

FIG. 3 is a cross section of the examination table of FIG. 2 taken at line 3-3;

FIG. 7 is an illustration of a 3D scan image display of a digital breast imprint overlay;

DETAILED DESCRIPTION OF A PREFERRED EMBODIMENT

Figure 1:
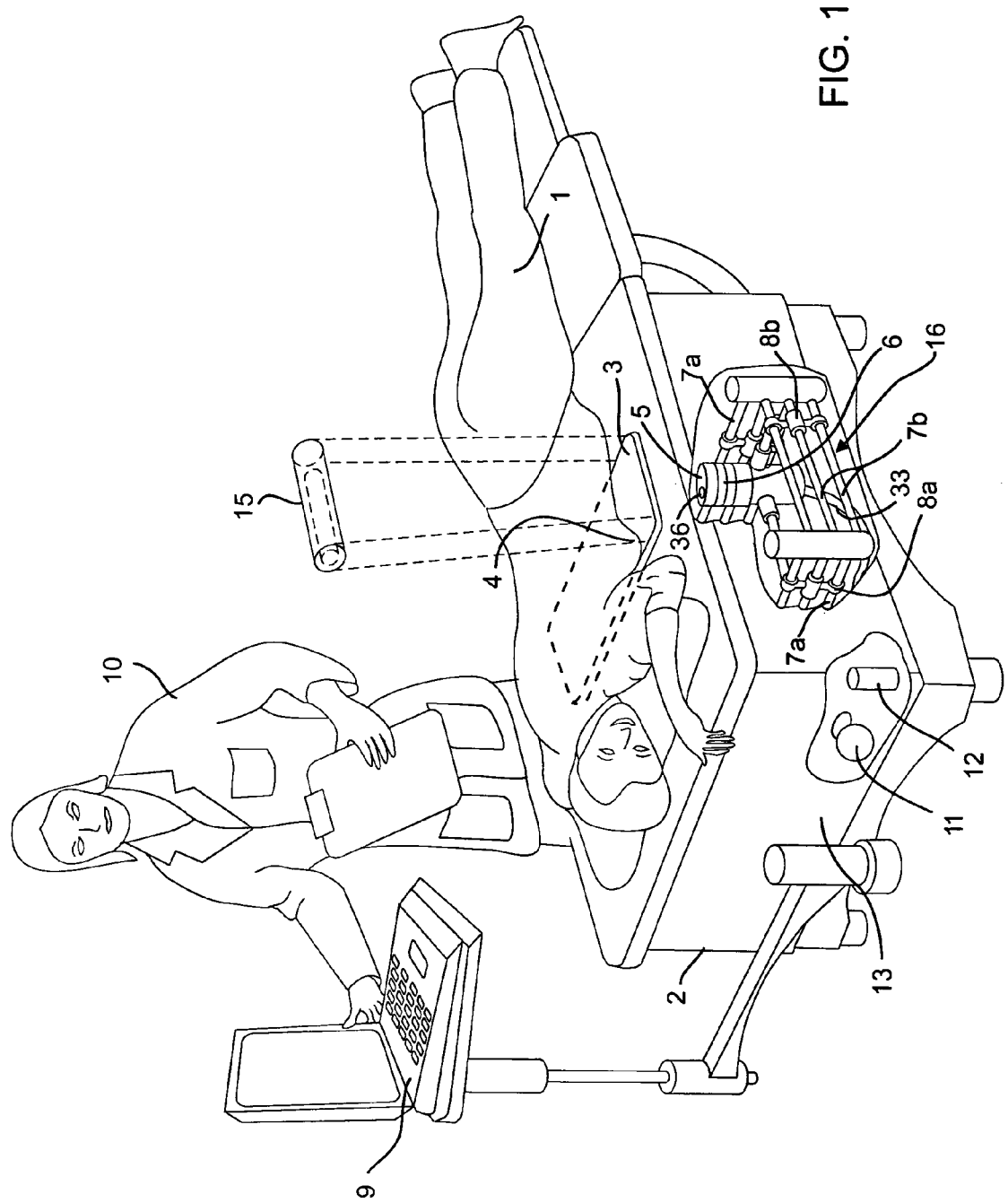
FIG. 1 is a perspective view of an examination table of the present invention in use, with portions broken away to show internal features.
Figure 8:
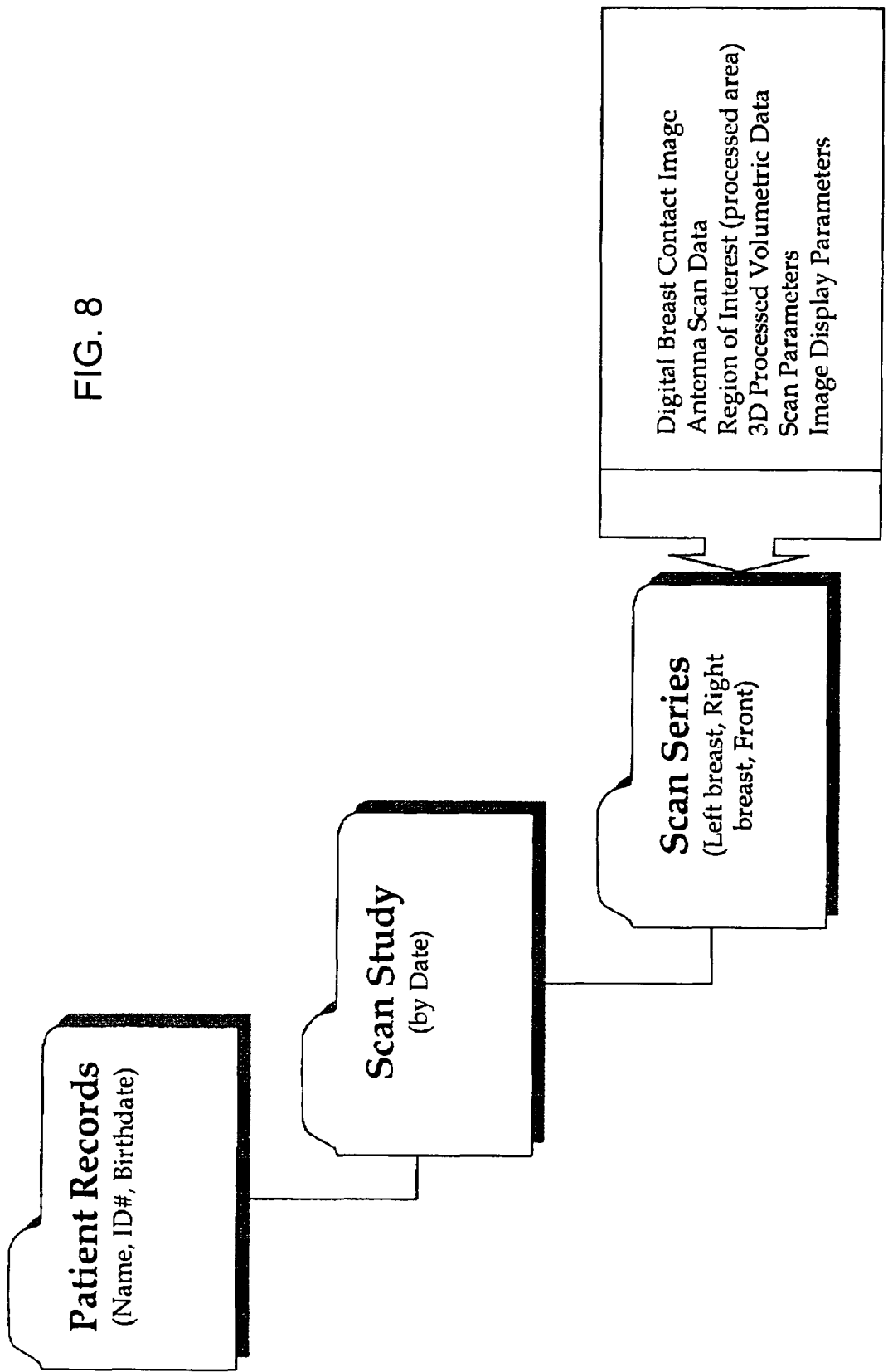
FIG. 8 is a flow chart of a scan system data archival structure.
Figure 9:
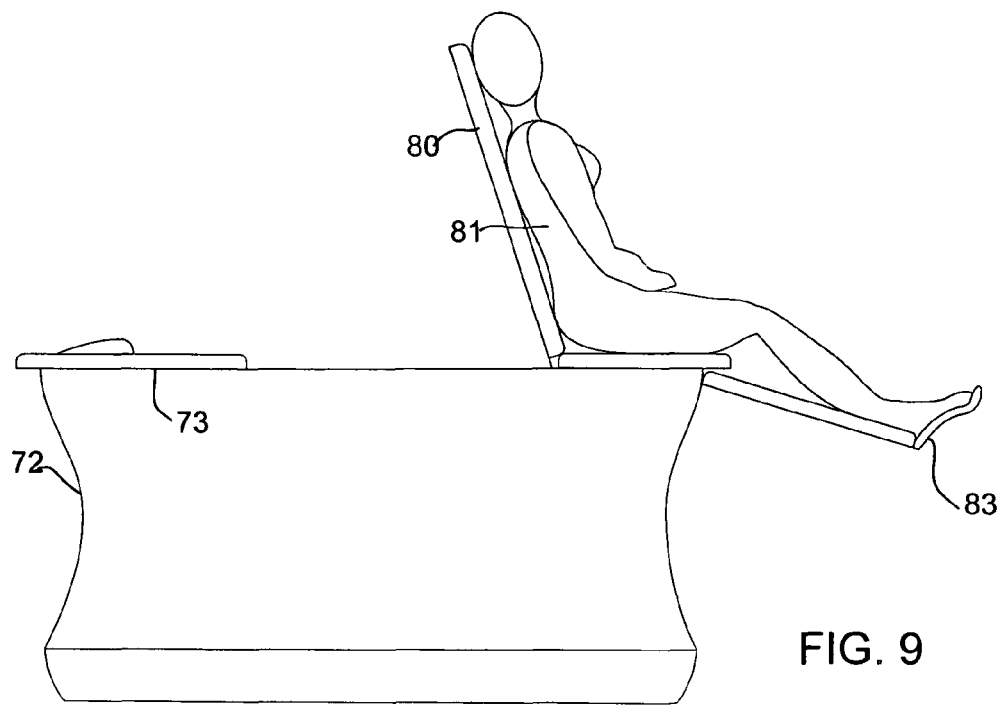
FIG. 9 is a side elevation view of an alternate embodiment of a multi-use examination table of the present invention.
Figure 10:
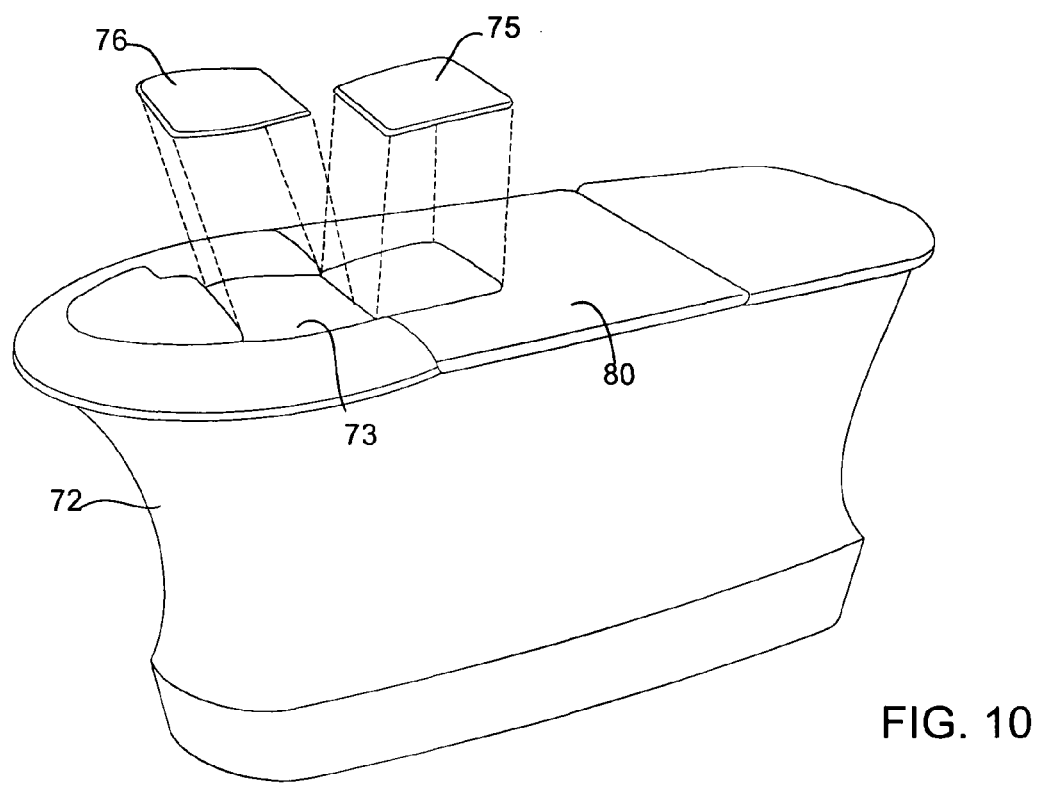
FIG. 10 is a perspective view of the examination table of FIG. 9.

An embodiment of the present invention is illustrated with reference to FIGS. 1-8. FIGS. 9-10 disclose an alternate embodiment discussed below. FIG. 1 illustrates a breast cancer radar screening system with a patient 1 lying prone on an examination table 2 of the present invention, with her breasts 4 pressed against a microwave and optically transparent scan plate 3. An upper horizontal face 5 of an antenna assembly 6 is in close proximity to the scan plate 3 with an air gap that avoids abrasion with the upper face 6 of the antenna assembly and also use of the scan plate 3 avoids contact with the patient 1. In an embodiment, the upper face 5 of the antenna 6 may be within approximately 1-3 mm of the scan plate 3.

A scanning subsystem 7a, 7b, 8a, 8b is located in an enclosure 16 formed within the table 2. The scanning subsystem 7a, 7b, 8a, 8b includes a motorized system that moves the antenna assembly 6 over the bottom of the scan plate in a predetermined pattern (see FIG. 5). A microwave source and receiver subsystem (not shown) is coupled to the antenna assembly to illuminate the breast via the antenna assembly 6 movement through specific locations on the scan plate 3 and collect the backscattered returns in a format suitable for digital signal processing.

Figure 4:
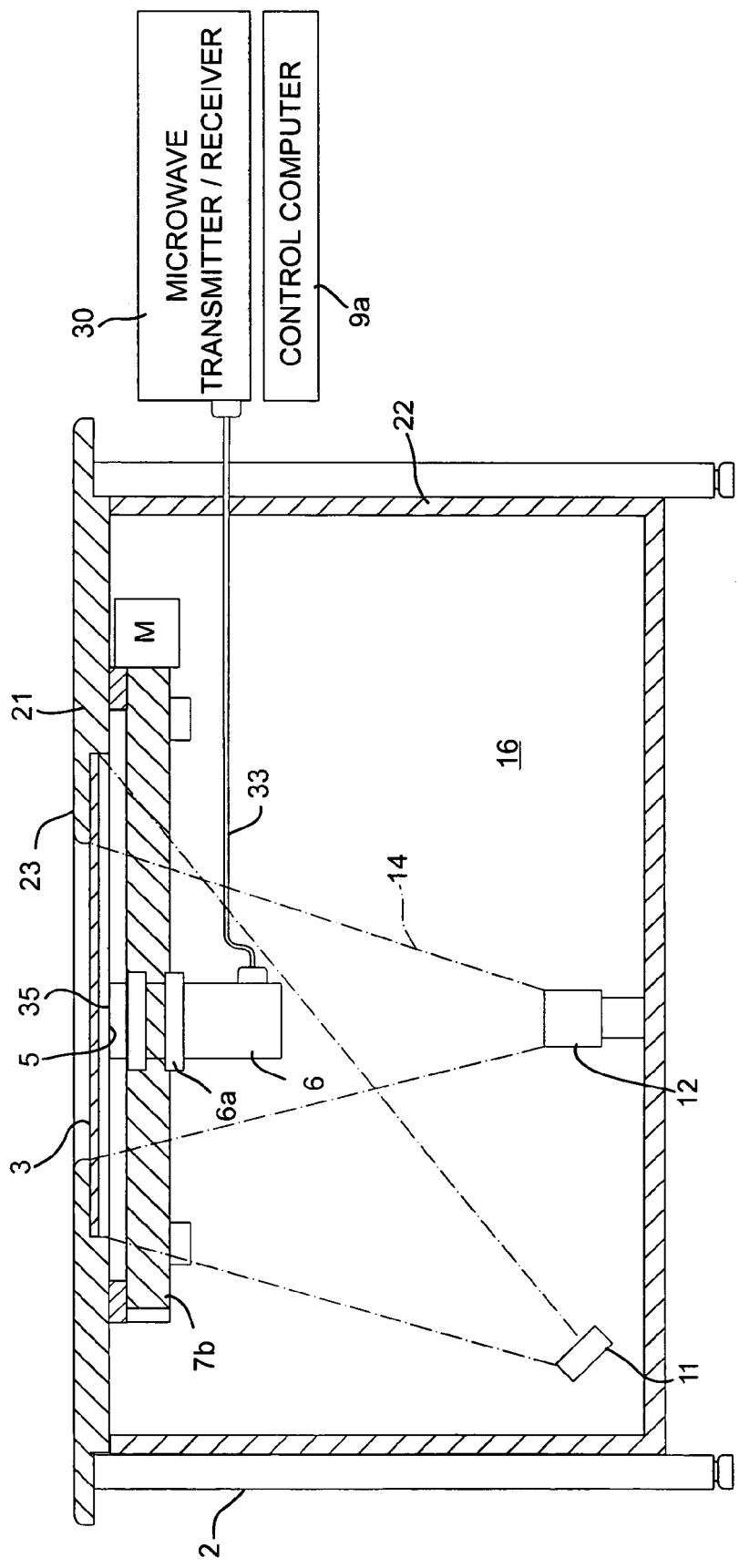
FIG. 4 is an enlarged cross-section of an examination table of the present invention disclosing an X-Y axis antenna gantry.

FIG. 2 depicts a plan view of the table 2 having the scan plate 3 located in the upper padded surface 23. FIGS. 3 and 4 represent the internal mechanical configuration of components within the enclosure 16 of the examination table housing 13. FIG. 3 depicts an embodiment of the present invention without a microwave antenna and FIG. 4 depicts an embodiment of the invention with an antenna 6. However, FIG. 3 includes microwave filtering devices, which in an embodiment are used with a table 2 such as that of FIG. 3 with a microwave assembly, such as a microwave antenna 6 incorporated therein. The housing 13 includes a light source, such as small visible flood lights 11 (Hampton Bay) that illuminate the imprints of the breast(s) on the scan plate 3. A digital camera 12 (Logitech Webcam Pix) provides imaging data from which the imprints of the breast 4 can be displayed, archived and recalled. The camera 12 includes a field of view 14 that encompasses the scan plate 3. FIGS. 3 and 4 illustrate the use of radio-frequency interference suppression materials 22 and the digital camera 12 arrangement. In an embodiment, the microwave assembly including the microwave antenna 6 and the camera 12 are connected to the same processor 9. However, in an alternate embodiment each system may have an independent processor 9, 9a.

Figure 6A:
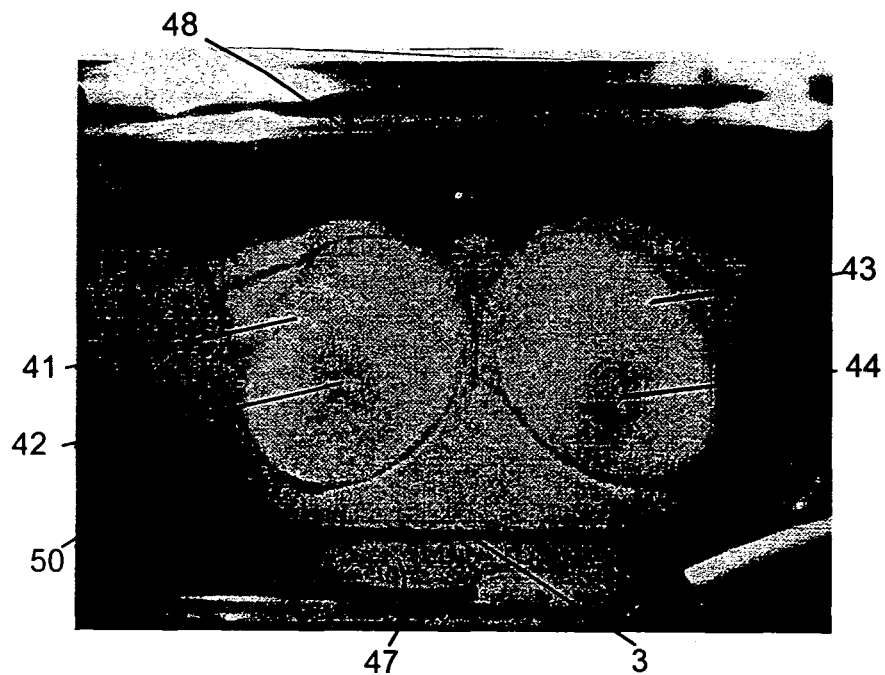
FIG. 6a is an actual digital image example demonstrating a typical frontal view imprint of both breasts of a patient.

The scan plate 3 receives the imprint of both breasts as illustrated in FIG. 6a, b. In an embodiment, the scan plate 3 is constructed of clear plastic material, such as cast acrylic, which is both optically and microwave transparent and can be several mm thick. The inside of the examination table, especially near the scan plate, is lined with radar absorbing material 22 (Emerson Cuming). The radar absorbing material suppresses the microwave resonances that may occur within the examination table 13. The apparatus may transmit ultrawide band RF pulses at frequencies as high as 10 gigahertz. Without this lining, the examination table might become a microwave resonant enclosure such that false indications might be developed.

In an embodiment, the upper surface 21 includes a microwave absorbent padding 23, 24 provided on the upperside metal surface of the examination table metallic top 28 and especially the area surrounding the scan plate 3. In an embodiment, the padding 23, 24 is formed from a microwave-absorbing foam (Emerson Cuming). The padding 23, 24 suppresses most microwave energy that could propagate between the torso of the patient 1 and the metallic top 28 of the examination table 2. Microwave-absorbing bean-bag-like pillows 15 (FIG. 1) or collars 24 can be used to help support the patient 1 and also to suppress any radio frequency energy that could propagate through the gaps between the edges of scan plate 3 and the torso, as shown in FIG. 1. Tubular pillows 15 may have a cylindrical core of microwave-absorbing foam. Various commercially available microwave filtering devices 25, 26 are available (Arcotronics, Captor, EMI Filter Company) to remove the microwave power from the external power line 25, from the data control cables 31 and from the air vents 29 (Chomerics Universal Air Filter).

A continuous envelop of metal, such as aluminum, can form the box-like structure 27 of the examination table 2, so that any microwave emissions are contained within the table 2. In an embodiment, the examination table 2 can be constructed of welded panels of aluminum or panels that can be joined by commercially available radio-frequency interference gaskets (Spira Manufacturing).

Also shown in FIGS. 3 and 4 are the electrical and microwave components that comprise the scanning subsystem. These include a vector network analyzer 32 (VNA) (Agilent ENA 5071), cables (not shown) that connect the VNA 32 with the antenna assembly 6, and an electrical isolation transformer 34 (ONEAC Model MD11 31). However, any type of microwave source transmitter and receiver 30 or computer controller 9a could be used, such as pulse source and sampling scope as noted in U.S. Pat. No. 6,061,589 which is incorporated by reference herein. The transmitter/receiver 30 is connected to the antenna 6 via cable 33. It is also to be understood that while "microwave" is used throughout this application to refer to the type of equipment, a wide range of transmission and receiver devices may be used to detect breast cancer according to the apparatus of the present invention. For example, devices having a range of 50 megahertz to 10 gigahertz may be used in the present invention. The present invention may also provide for scanning using infrared equipment.

X-Y traversing equipment is depicted in FIGS. 1 and 4 including gantry subassembly 7a, 7b, 8a, 8b, which moves the antenna subassembly just beneath the scan plate 3. Components for such mechanical scanner are commercially available and can be assembled into a complete X-Y scanning system as described in U.S. Pat. No. 4,641,659. The subassembly includes X-axis gantry 7a, 8a and Y-axis gantry 7b, 8b. Techniques to identify the position of the antenna digital or analog format are well known and are also described in detail in U.S. Pat. No. 4,641,659, which is incorporated by reference herein. Such components include stepping or servo motors, lead screws, carriages, ball slides, tracks, motion controller and power amplifiers. Currently available components might include the AAICK MD-2 scanner, the Galil 1822 power amplifier and the Applied Motion Products PE03540 controller or other off the shelf actuators and motion control products. To ensure the integrity of the transmitted signal and the measured returns, the transmission lines and cables 33 running between the microwave source, antenna and receiver must be kept as short and as straight as possible.

The scan plate 3 can be comprised of many commercially available glasses or plastics that are listed in Von Hippel, Dielectric Materials and Applications, MIT Press-Wiley. In an embodiment, the scan plate 3 will have both optical and microwave transparency. In the microwave band of 1 to 10 GHz the dielectric properties should be matched. When the relative dielectric constant can range from 1.7 to over 9, the path absorption over about 3 to 6 mm is less than a few dB. Scan plate optical properties should not have a path loss of more than a few dB, and preferably should be less but greater values may be acceptable, provided breast imprints are seen. Other suitable materials could also be polystyrene, polycarbonate, and cast acrylic (Lucite, Plexiglas). A wide range of materials that are microwave and optically transparent with dielectric values, 1.5-5 are widely available and can be used with the confocal, pulse type imaging systems such as described in U.S. Pat. No. 5,807,257. Pulse type, wide band imaging system have been demonstrated to be able to gate out any backscatter from mismatches between the dielectric properties of the breast tissue and the scan plate.

FIG. 4 represents the antenna face 5 arrangement to the scan plate 3 with a non-contact air gap 35 in order to eliminate the antenna 6 from scraping against the scan plate during X-Y travel. The microwave scanning system and antenna design allows for minimal air gap 35 without disturbance to scan data. The fixed air gap dimension provides stable scan measurement returns of data necessary for digital image processing. Alternatively, the constant air gap can be maintained through the use of a Teflon bushing 36 (FIG. 1) between the antenna face and scan plate 3. Through the use of a semicompliant antenna mount 6a, the bushing 36 would maintain consistent contact with the scan plate under patient load.

In an embodiment, the constant air gap spacing can range from 1 to 3 mm without materially perturbing the propagation pathway from the antenna faceplate 5 to the scan plate 3. This is possible because the wavelength in air is 50 mm at the highest frequency of 6 GHz. Using a transmission line model, an air gap of 1 to 3 mm equates respectively to 2-6% of the wavelength. If the air gap spacing were to be a sizable fraction of the wavelength ($\frac{1}{8}^{th}$ or more), the pathway reflections and wave divergence perturbations would occur. To compensate, the signal processing circuits could be used to partially mitigate the signal degrading perturbations.

Figure 5:
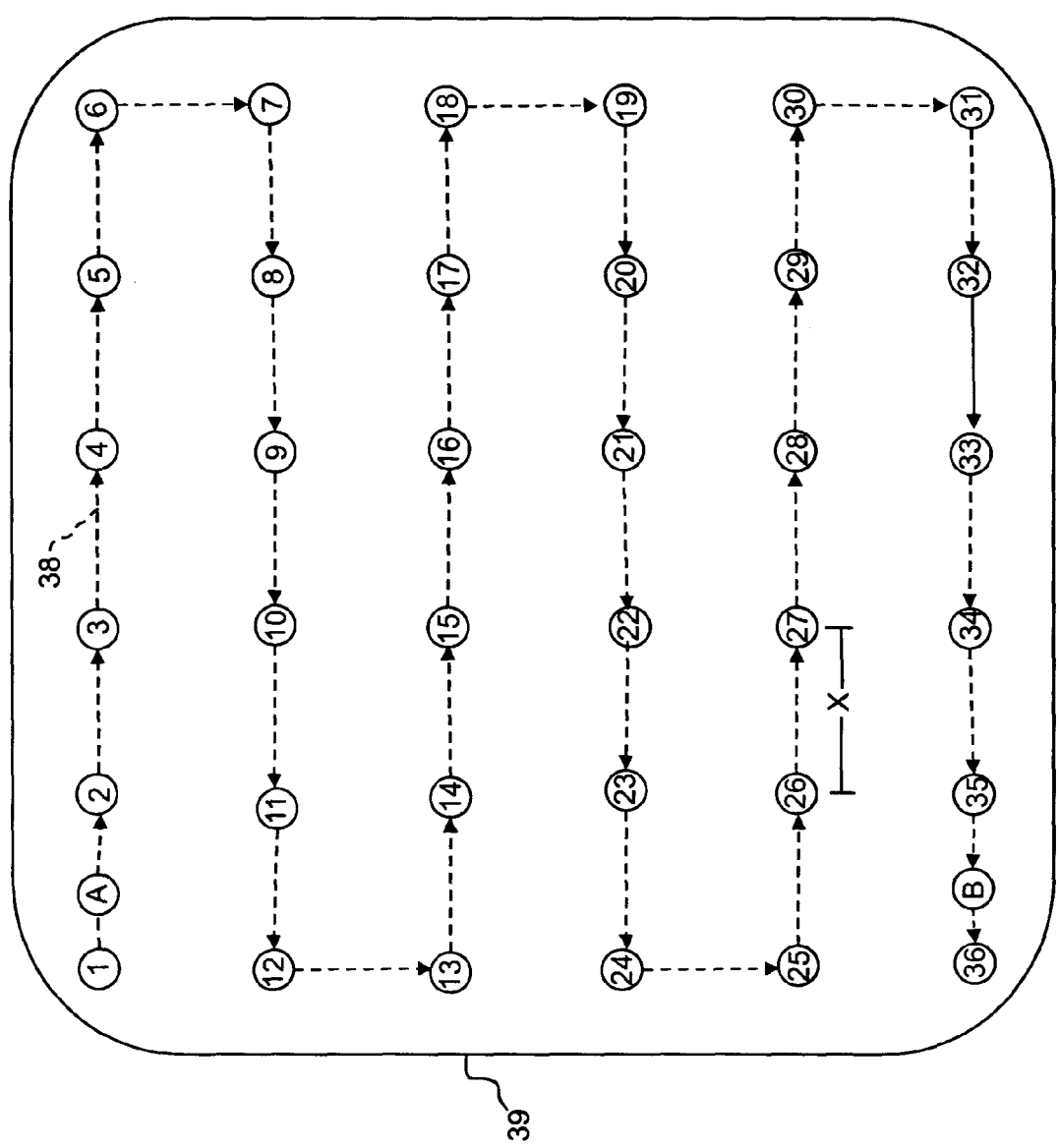
FIG. 5 is an illustration of the tracking movement of the antenna of the present invention.

To accomplish efficient movement and operation of the antenna, the breast cancer radar screening system employs an X-Y gantry 7a, 7b, 8a, 8b to move the microwave equipment and the indexing antenna elements 6 maintaining a trajectory that minimizes the distance the discretely indexing antenna element 6 must move, as shown in FIG. 5. The antenna moves generally in a continuous rectilinear tracking pattern 38 (dashed line) generally between points A and B. The antenna is controlled during such tracking to locate its waves on scan points 1-36 along a scan path 38. While moving continuously, the antenna is traversed through a discrete number of locations. It is noted that FIG. 5 is only an illustrative example of the tracking path 38 and In an embodiment, there are more than 1500 scan points and the path may be different. The scan path 38 periphery generally defines a scan envelope 39. In an embodiment, scan point spacing between each set of scan points is a uniform distance X. For example, between scan points 28 and 27, X is approximately 1 cm.

The relative coordinates of the antenna positions within the scan envelope 39 define a surface in two dimensions (X-Y antenna plane) used by the present system's post processing to generate a scan image 92 (FIG. 7) of the internal breast volume behind the surface of the scan envelope.

Movement of the envelope of the antenna element 6 is defined for each patient, through the use of the digital camera 12. A Set Scan Envelope application running on personal computer 9 operates the X-Y discrete indexing antenna positioner 7a, 7b, 8a, 8b. The antenna 6 movement may be constrained to the patient breast imprint, as defined by the set scan envelope. Radio frequency energy that is emitted by the antenna 6, and not reflected to form the image, is highly attenuated by the patient's body 1.

In an alternate embodiment, the antenna may also stop at each scan point 1-36. This may be accomplished through the use of an X-Y discrete indexing antenna gantry 7a, 7b, 8a, 8b capable of indexing the antenna 6 through a series of discrete positions across the X-Y antenna surface and spaced 1 cm apart, pausing at each position long enough for a series of microwave signals to be transmitted and their return echo recorded (approximately 1 second). The X-Y gantry provides a means to maintain a predetermined, fixed, spacing between the antenna positions and the skin of the breast.

Figure 6B:
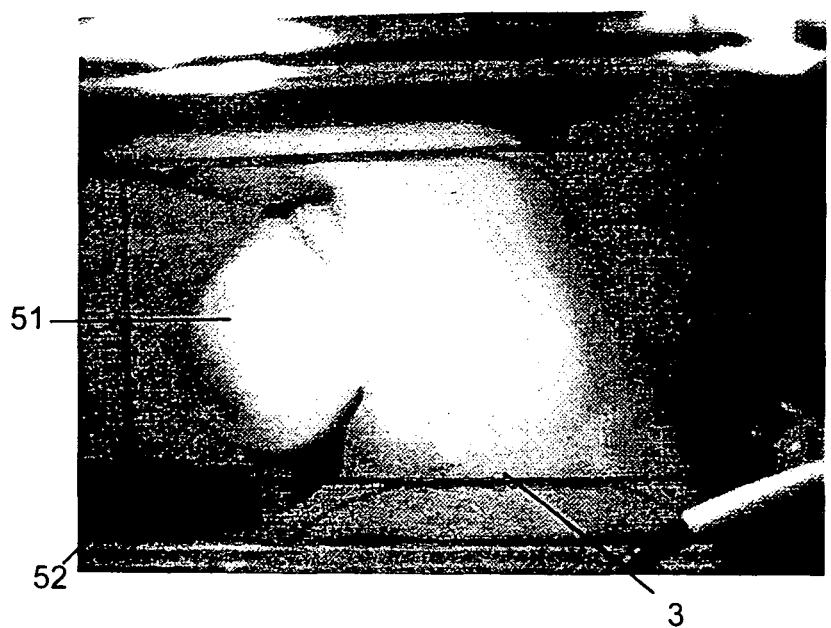
FIG. 6b is an actual digital image that is a side view of the imprint of a breast and armpit of a patient.

FIGS. 6a and 6b respectively show the full front imprint of both breasts and a side imprint near the armpit. FIG. 6a shows the right breast 41; the right nipple-areola 42; the left breast 43 and the left nipple-areola 44. Also shown is the transparent scan plate 45; the interface 46 between the torso or breast and the top of the examination table. The lower torso 47 and upper chest 48 are also shown. A portion of hospital gown sometimes may appear in the digital photo image. Uncovered gaps 50 between the torso and the examination table are also shown. Such gaps 50 may be covered by the pillow 15, such as shown in FIG. 1. FIG. 6b shows the side or auxiliary breast imprint 51, the nipple-areola 52 and the scan plate 3.

The scanning system control subsystem encompasses a personal computer 9 keyboard display and computer programs. In addition to the control of the scanning system, the software collects, manipulates, displays and stores scan data (as shown in FIG. 8). These control the operation of all of the equipment, process the scan returns display the image and archive the data. In an embodiment, the scanning control subsystem computer program may be operated through an operating system such as Windows XP.

In an embodiment, the system comprises a User Interface and Control Layer and a Device Control and Processing Layer. The User Interface and Control Layer includes Administrative Applications, Device Control Applications, Image Display Applications and Archival Applications.

The Administrative Applications include Boot-Up, Calibration, Valid Forward/Authorization procedures and diagnostics. The Device Control Applications include Initialized Scan, Capture Scan Image, Set Scan Envelope, Perform Scan, Re-do Scan and End Scan procedures. The Image Display Applications include Set Forward/Adjust Processing parameters, Display Scan Results and Reprocess Scan Data. The archival applications include Print Scan Results, Save Scan results, (local)/(remote), Save Scan data (local)/(remote), Transmit Scan data/results and Archive Scan data/results (local)/(remote).

The Device Control and Processing layer includes Device Control and Data Collection Applications, Signal and Return Processing Applications, Imaging Display and Manipulation Applications, and External Interface Applications. The Device Control and Data Collection Applications include X-Y Motion Control, Microwave send/receive, Return Data Format and Photo Image Capture. The Signal and Return Processing Applications include Frequency-to-Time Convert (Fourier transform) and time-to-3D construct. The Image Display and Manipulation Applications include 3-Space Interpolation, Shape/envelope Build and 3D Display and Manipulation. The External Interface Applications include PACS Interface, Network Printing, Data Transmit, Display Application Distribution and Processing Application Distribution.

The User Interface & Control Layer architecture and applications, running on a personal computer 9, presents the applications and control parameters to which operating technicians 10 will have access. The Device Control & Processing Layer architecture and applications, control the individual system components, captures the return data, generates the scan image and interfaces with external devices and networks. The overall scan envelope, and the coordinates of each antenna position within the scan envelope, are established and controlled through the Device Control applications of the User Interface & Control Layer and the Device Control & Data Collection applications of the Device Control & Processing Layer. The proprietary signal processing and image display applications are used to filter noise, reconstruct the imaged data space and present the final image.

The present invention may provide accurate scan data whether the patient has a thin garment, such as a hospital gown, covering her breasts or if her breasts are bare when positioned on the scan plate. This is feasible because the patient's breasts 41, 43, 51 (and gown) maintain stable contact with the scan plate 3 for the duration of the scan. This stability enables the Signal & Return Processing applications, within the Device Control and Processing Layer, and the Image Display Applications, within the User Interface and Control Layer, of the software architecture to factor out the return signal distortions attributable to the intervening garment and produce a consistent and useable image. While the scan data may be accurate with clothing, it is preferable that the breasts 41, 43, 51 be bare when photo imaging of the breasts is provided for the digital breast imprint overlay image (FIG. 7), so that the location of the tumor may be more easily located with reference to breast markings, such as the nipple 42, 44 (which may not be visible if the patient has a hospital gown covering her breasts).

The discrete indexing of the antenna through a standard set of positions provides a coordinate reference frame that is reproducible across scans. The matched antenna coordinates and signal return data are passed to the Signal & Return Processing applications of the PC/Signal processing architecture & applications of the PC controller. Proprietary signal processing algorithms within the Signal & Return Processing applications are capable of filtering the signal distortions caused by intervening scan plate 3. The anomalies detected by the system are clearly highlighted, and the spurious returns are highly suppressed. The ability of the system's parametric Image Display & Manipulation Applications, running in conjunction with the dynamically adjustable Image Display Applications generate repeatable, unambiguous images readable by medical laymen without the need for extensive training and specialized interpretive skills.

User interfaces, such as, keyboard, general pointing devices (e.g. mouse and/or touch screen monitor) aid in the control and manipulation aspects of the device operation and control, including interfacing the personal computer 9 with the technician 10. The operator 10 has an option to invoke the Set Scan Envelope application within the User Interface & Control Layer and uses the image presented on the PC controller screen to outline the desired scan envelope (the area to be scanned).

FIGS. 9-10 discloses an alternate embodiment of an examination table 72 having design features that allow for multi-use general practice examinations beyond breast scanning. The scanning table 72 can be easily used as a general examination table by covering the scan plate 73 with equivalent pad cover 76 that is put in place. Additionally, the pad 80 adjacent the scan plate 73 can be raised to an incline for raising the patient's 81 torso when needed. Self storing stirrups 83 for supporting patient feet during gynecological exams are also available within the scanning examination table 72. These features are important to physicians who wish replace existing examination tables with the scanning tables 72 due to office space constraints.

The examination table 72 pad design has incorporated several features to provide optimal patient comfort and breast alignment necessary for accurate scanning. Changeable torso pads 75, 76 with varying shapes such as tapered shapes, and varying thickness provide both comfort and proper breast compression for varying patient breast sizes. The pad 75, 76 may have a tapered shape to provide proper patient breast contact, especially for side scans. Pressure felt from the contact between the scan plate 3 and breast 41, 43 (FIG. 6a) is minimized by recessing the scan plate into the table top at a depth of 4-6 cm, or by orienting a tapered pad 75, 76 in order to raise or lower the patient's torso enabling breasts of all sizes of the size spectrum to be effectively and comfortably scanned. Additional pillows 15 (see FIG. 1) are also provided for the technician 10 to use for additional patient comfort where needed. Proper patient comfort and support are important in providing accurate scans requiring several minutes of steadiness of the imprint.

To initiate a scan, the operating technician first assists in positioning the patient 1 onto the examination table. The technician inputs the appropriate patient data into the system via the keyboard 9 (FIG. 1). Next, if the scan is for the front view of both breasts (FIG. 6a), the technician invites the patient to take a prone position (as shown in FIG. 1) and to place both breasts onto the scan plate (FIG. 6a). The technician 10 may include a doctor, nurse, physicians assistant, therepast or other medical personnel. The technician operates a support system provided by the examination table of the present invention in order to support the patient's breasts comfortably in a fixed position while the patient is lying on the table 2. The support system includes all elements discussed above that assist in the support of the patient and the patient's breast(s), such as, the pillow 15, the padding layer 23 of the upper surface of the table, the collar 24, the pads 75, 76 or the scan plate 3. By arranging these members of the support system, the technician may provide the patient's body and her breasts in a fixed position so that her breasts may be scanned properly. The present invention provides for a patient's breast to be supported in a fixed position by using only one member of the support system, or by utilizing many members or pieces of the support system. For example, it may only be necessary for the technician to position the breast with respect to the scan plate 3 in order to get a proper scan and achieve a comfortable and fixed position of the breast. In other situations, in addition to the scan plate, the technician may have to place a pillow 15 next to the patient in order to achieve a comfortable and fixed position of the breast.

The technician then uses an orientation system of the present invention in order to further orient the patient and patient's breast to insure proper scanning. The orientation system includes all elements described above that assist in the orientation of the patient and the patient's breast(s), such as, the microwave assembly comprising of the microwave antenna 6, processor 9, control computer 9a, transmitter/receiver 30, VNA 32 and transformer 34, the light 11, camera 12, digital imaging system and scan data system and applications. The orientation system provides for orientation of the breast in known positions with respect to the anatomy of the patient and locations of the antenna 6. For example, the orientation system may provide for scan data with respect to the patient's anatomy, such as, breast tissue, nipples, armpit, sternum or lesion. The technician uses the orientation system to further position the breasts on the scan plate 3. For example, the technician may view the position of the breasts on the scan plate 3 by activating the live digital camera 12 and viewing the image on the computer monitor 9 that displays the imprint of both of the breasts (FIG. 6a). If the arrangement is not satisfactory, the technician 10 helps the patient 1 to reposition her breasts as needed.

Depending on the imaging system, the technician, using the visual display of the breast and the mouse, can identify the areas of the breast to be illuminated (scanned) by the antenna 6. Although slower than the visual image provided by the camera 12, the technician may separately rely on the scan data from the antenna 6 in order to determine if the patient's breasts are properly oriented. If needed, the technician also arranges the microwave-absorbing pillows 15 to cover the areas on the scan plate 3 that are between the torso 47 or breasts 41, 43 and the open gaps or edges 50 of the scan plate 30. Similar positioning is provided for scans of a side of the breast. In an alternate embodiment, a window may be formed in a side of the table 2 and a mirror positioned so that positioning of the breast(s) on the scan plate 3 may be observed by the technician 10 through the window.

After positioning the patient for scanning, the live photo image is captured digitally by the use of the digital camera 12. The antenna 6 is moved to the periphery of the scan envelope 39 so that it is at the edge of the field of view so that the antenna 6 is not blocking the view of the breast imprint on the scan plate 3 and an unobstructed photo image may be obtained. This photo image is stored for use as an overlay 90 to the 3D scan image generation 92 provided by the processed scan data, as will be discussed below.

By use of a computer pointing device (e.g., touching the screen, mouse or activating a switch) the scanning procedure can be initiated. First, the scanning subsystem begins the scan with the antenna 6 being excited by a microwave source. At known locations (see FIG. 5), the antenna illuminates the breast via the antenna 6 and collects the backscattered returns in a format suitable for digital processing by the digital computer 9. When the scan is completed, the scan data is processed to form a 3D scan image. The resulting data and display images are archived, including the data for the visual display as shown in U.S. Pat. Nos. 5,829,437 and 6,061,589, each of which are incorporated herein by reference.

The preferred system is especially useful when used in conjunction with the pulsed, confocal, microwave 3-D imaging systems described in U.S. Pat. No. 5,704,355 or U.S. Pat. No. 5,807,257 or U.S. Pat. No. 5,829,437, each of which are incorporated herein by reference. Possible versions of these systems could have the antenna 6 continually move or pause at each antenna position 1-36 (FIG. 5), transmit and ultra wideband pulse and collect the backscatter. The return data from each antenna position, relative to locations on the surface of the breast 41, 43, 51 is processed to form a 3-D scan image 92 (FIG. 7). The stability of the surface of the breast 41, 43, 51 relative to the locations of each antenna position 1-36 must be stabile within $\frac{1}{8}^{th}$ to $\frac{1}{4}^{th}$ of a wavelength of the highest frequency in normal breast tissue. Assuming that the highest frequency is 6 GHz and the dielectric constant is 9, $\frac{1}{8}^{th}$ of a wavelength is 2 mm.

Knowing the coordinates of each antenna position 1-36 (relative to the other antenna positions), as the antenna 6 is pulsed and the location of each antenna position relative to the surface of the breast 41, 43, 51, the backscatter returns from a postulated location within the internal breast volume can be constructively combined to determine whether or not a lesion 99 exists at the postulated location.

As shown in FIG. 7, the photo image overlay 90 provides a visual orientation of the breast image with respect to the patient anatomical features, such as, the nipples 42, 44. In an embodiment, the photo image 90 alignment to the 3D generated scan image envelope 92 is provided during the machine manufacturing prior to delivery. In an alternate embodiment, alignment of the photo image 90 to the scan image envelope 92 may be accomplished by a technician via the processor 9. The center of digital camera field of view is sized and aligned to the 3D generated scan image envelope top center 94. The aligned photo image 90 becomes an overlay on the top of the 3D generated scan image envelope 92 (the top planar envelope) with origin (0,0,0) at top center 94. This alignment provides dimensional alignment within millimeter accuracy. The accuracy provides scaling that can be displayed in Cartesian coordinates including X axis 95, Y axis 96 and Z axis 97 on the 3D image 92 that pinpoint a lesion image 99. The displayed coordinate scaling assists the physician during the scan review process. To further enhance the clinical relevance of the image, the breast cancer radar screening system superimposes the digital photo image 90 of the breast contact area on to the top surface of the three dimensional scan image 92 generated by the Image Display applications. The composite 3D scan image 92 may be rotated using known software graphics tools so that the photo image 90 of the breast contact area remains intact on the "top" surface of the scan envelope 92 (the top planar envelope) in order to provide the clinician with a point of orientation and frame of reference for the clinician beyond the simple text labels used for each axis 95, 96, 97.

Other combinations of visual display methods of the location of the breast relative to the microwave illumination methods or antennas are possible. For example, phased arrays of waveguide antennas could be mounted below an optically and microwave transparent plate. To position the breasts, the waveguide array could be shifted away such that the breast imprint would be visible and illuminated as described earlier. The waveguide array would then be shifted to almost touch scan plate. Alternatively, reasonable imprints might be visible through the spaces between each waveguide antennas that are pressed against or penetrates through the scan plate. Various combinations of illuminating and light collecting optical glass fibers could be used if an optically opaque mounting of the phased array antennas is used. In this case, pairs of fiber bundles would be arranged between the interstices of the waveguides. One bundle would illuminate and the other bundle would carry the backscattered light into a display that would indicate the position of the breast.

In this patent, the term, "tumor" can be a lesion or be either benign or malignant. This term also includes other anomalies, including scar tissue, regions of high vascularization, and foreign material, such as clips, staples. Further, the methods and apparatus noted here have been described in context of an examination table that could be modified to suppress unwanted microwave interaction. However, the signals used by some systems are so small and intermittent that such containment measures may not be needed. Other configurations that use the optical imprinting, patient positioning and microwave penetration and reflection techniques can be used for specialized situations without the need for a complex examination table. The term "optical" includes energy in the near infrared and visual spectrums and microwave generally includes frequencies ranging from 0.1 GHz to 100 GHz but can include induction fields from much lower frequency sources Therefore, it may be understood that the following features are provided by the present invention. The patient is made comfortable and is able to hold a fixed position in the order of a few minutes until the scan is completed. The examination method may include both breasts as well as areas near both axilla or armpits. The position or surface of the breast is known within a few mm with respect to the anatomy of the patient as well as to the antenna locations or characteristics of the illumination pattern. The clinical technician is able to assist the patient to properly position her breasts, such that all volumes of the breast are illuminated, in separate scans as needed including both the frontal regions near the nipple as well as those near the armpits. The above positions are able to be photo recalled. The scanning can be performed without direct patient contact to the antenna. The examination table is easy to operate. Spurious radio frequency emissions or susceptibility is suppressed. The examination table can house all of the microwave and electronic equipment and provide for power, data transfer, and cooling while suppressing spurious RF leakage outside of the examination table. The examination table is suitable for use in both hospitals or in the facilities of primary care physicians.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. An apparatus for screening or diagnosing cancer or other pathological disorder in a breast of a patient comprising:
   a table having a horizontal upper surface upon which the patient may lie;
   a support system adapted to support the patient comfortably and to directly contact and support the patient's breast in a fixed position while the patient lies in a prone position on the table;
   a microwave assembly including a microwave source, a microwave antenna and a receiver, the microwave source coupled to the microwave antenna for directing a predefined microwave waveform to the breast, the receiver coupled to the antenna for receiving reflected microwave energy from the breast under examination resulting from the predefined microwave waveform; and
   an orientation system for orienting a surface of the breast in known positions with respect to the anatomy of the patient and locations of the antenna; and
   a processor connected to said receiver for processing the reflected microwave energy.

2. The apparatus of claim 1 wherein the support system includes a microwave-transparent scan plate carried by the table located at the upper surface so that a portion of the breast may be pressed against the scan plate.

3. The apparatus of claim 2 wherein the scan plate is optically transparent and the orientation system further comprising:
   a light source oriented to transmit light through the scan plate in order to optically illuminate the breast;
   a camera for capturing a visual image of the breast and transmitting said image to the processor; and
   means coupled to the processor for displaying an image including the visual image.

4. The apparatus of claim 3 wherein the orientation system further includes a scan data system for providing a scan image from the reflected microwave energy, the scan data system connected to the processor and a display for displaying the scan image of the reflected microwave energy.

5. The apparatus of claim 4 wherein the orientation system further includes means for displaying an overlay of the visual image and the scan image of the reflected microwave signal.

6. The apparatus of claim 1 wherein the orientation system further includes a scan data system for providing a scan image of the reflected microwave energy, the scan data system connected to the processor and a display for displaying the scan image of the reflected microwave energy.

7. The apparatus of claim 2 wherein the scan plate has a dielectric constant in the range of from about 1.7 to about 9.

8. The apparatus of claim 5 wherein the overlay image is a composite 3-D image.

9. The apparatus of claim 2 wherein the position of the breast with respect to known antenna position on the scan plate that is stable within approximately ¼th of a wavelength of the highest frequency.

10. The apparatus of claim 2 wherein an air gap of approximately 1 mm is provided between the microwave antenna and the scan plate.

11. The apparatus of claim 1 further comprising:
    an enclosure that is formed as part of the table and that encompasses the microwave assembly.

12. The apparatus of claim 7 including means for suppressing microwave resonance within the enclosure.

13. The apparatus of claim 1 further comprising a microwave-absorbent resilient member located adjacent the scan plate and interposed between the scan plate and the surface of the table.

14. The apparatus of claim 7 wherein the microwave-absorbent resilient member is a bag-like pillow.

15. The apparatus of claim 7 wherein the microwave-absorbent resilient member is a collar.

16. The apparatus of claim 7 wherein the microwave-absorbent resilient member forms a padding layer on the upper surface of the table.

17. The apparatus of claim 1 wherein the processor is provided by a personal computer connected to the table.

18. The apparatus of claim 17 wherein the personal computer provides a display.

19. The apparatus of claim 17 wherein the processor is incorporated with the table.

20. The apparatus of claim 1 wherein the orientation system includes a means for viewing the breast when in the fixed position.

21. The apparatus of claim 20 wherein the viewing means is a digital camera.

22. The apparatus of claim 1 further comprising a motorized system for moving the antenna along coordinates.

23. The apparatus of claim 1 wherein the table includes an adjustable upper surface section to aid the patient to sit upright.

24. The apparatus of claim 1 wherein the table includes a removable pad.

25. The apparatus of claim 24 wherein the removable pad covers the support system.

26. The apparatus of claim 24 wherein the removable pad includes a taper in order to appropriately elevate the patient's torso in order to comfortably locate the breasts on the support member.

27. The apparatus of claim 24 wherein the removable pad is provided in an adjustable upper surface section of the table.

28. A method for imaging or detecting breast lesions comprising the steps of:
    having a patient lie prone on a table having a microwave and optically transparent scan plate;
    pressing a patient's breast against the scan plate to support the patient's breast in a fixed position;
    illuminating the patient's breast through the scan plate;
    receiving a visual image of the breast by a digital camera;
    directing a predefined microwave waveform to the breast;
    receiving reflected microwave energy resulting from the predefined microwave waveform to produce scanning data;
    processing the scanning data based on reflected microwave energy; and
    forming a displayed image including the visual image and the scanning data.

29. The method of claim 28 wherein a pair of breasts are imaged.

30. The method of claim 28 wherein the patient is oriented in order to provide a frontal imprint of the breast.

31. The method of claim 28 wherein the patient is oriented in order to provide a side imprint of the breast near the patient's armpit.

32. The method of claim 28 further comprising the step of archiving the displayed image.

33. The method of claim 32 wherein the archiving includes a patient record, scan study data and scan series data.

34. The method of claim 33 wherein the scan series data includes a digital breast contact image, antenna scan data, region of interest data, 3D processed volumetric data, and scan parameters or image display parameters.

35. The method of claim 28 further comprising the step of analyzing the displayed image and reorienting the patient in order to provide the breasts in appropriate orientation.

36. The method of claim 35 wherein the analyzing is performed by a human viewing the displayed image.

37. The method of claim 28 further comprising the step of identifying areas of the breast to be scanned by the antenna.

38. The method of claim 37 wherein the identifying step is performed by a human using a computer mouse of a computer having the displayed image.

39. The method of claim 28 further comprising the step of orienting a microwave-absorbent resilient member adjacent the patient in order to cover a gap formed on the scan plate that are adjacent the breast.

40. The method of claim 39 wherein the microwave absorbent resilient member is a bag-like pillow.

41. A method for imaging a lesion comprising the steps of:
orienting a patient's breasts on an optically transparent scan plate to provide an imprint;
focusing a digital camera on the imprint, the digital camera having a field of view;
directing a predefined microwave waveform to the breasts;
generating a 3D generated scan image of the breasts using reflected microwave energy from each breast independently resulting from the predefined microwave waveform, the scan image having a top planar envelope;
sizing the field of view to match the size of the top planar envelope;
generating a photo image of the imprint having the sized field of view;
aligning the sized field of view with the top planar envelope; and
overlaying the photo image on the top planar envelope.

42. The method of claim 41 wherein the 3D generated scan image includes a graphical image of a lesion that is visually oriented to the imprint envelope of the patient's organ.

43. The method of claim 41 wherein the overlay is aligned to an origin point (0,0,0) on the top planar envelope.

44. The method of claim 41 wherein the 3D generated scan image includes Cartesian coordinates in the X, Y and Z planes.

45. The method of claim 41 wherein the organ is a breast and the imprint is provided on the scan plate mounted in an upper surface of an examination table.

46. An examination table comprising:
a table having a horizontal upper surface upon which the patient may lie;
a support system adapted to support the patient comfortably in a fixed position;
an orientation system for orienting a patient's torso in known positions with respect to the anatomy of the patient;
an optically transparent scan plate affixed to the table and located at the horizontal upper surface;
a light source oriented to transmit light through the scan plate in order to optically illuminate the torso;
a camera for capturing a visual image of the torso and transmitting said image to a processor;
a scan system for directing a predefined microwave waveform to a portion of the patient and for receiving reflected microwave energy resulting from the predefined microwave waveform; and
means coupled to the processor for displaying an image including the visual image of the torso's imprint.

47. The apparatus of claim 46 wherein the support system includes an adjustable upper surface section to aid the patient to sit upright.

48. The apparatus of claim 46 wherein the support system includes a removable pad.

49. The apparatus of claim 48 wherein the removable pad covers a scan plate carried by the table.

50. The apparatus of claim 48 wherein the removable pad includes a taper in order to appropriately elevate the patient's torso in order to comfortably locate the torso on the scan plate.

51. The apparatus of claim 48 wherein the removable pad is provided in an adjustable upper surface section of the table.

52. The apparatus of claim 46 wherein the orientation system provides scan data regarding the patient's breast with respect to at least breast tissue, a nipple, a sternum, an armpit or a lesion.

* * * * *